United States Patent [19]

Porcello

[11] Patent Number: 6,019,941
[45] Date of Patent: Feb. 1, 2000

[54] METHOD FOR DISINFECTING DERMAL SURFACES AND INANIMATE SURFACES, AND PARTICULARLY AIR DUCTS

[76] Inventor: Joseph A. Porcello, 2600 S. Ocean Blvd., A3, Boca Raton, Fla. 33432

[21] Appl. No.: 08/593,615

[22] Filed: Jan. 30, 1996

[51] Int. Cl.⁷ .................................................. A61L 9/14
[52] U.S. Cl. .............................. 422/4; 422/37; 424/667; 514/731
[58] Field of Search .................. 422/4, 37; 424/667, 424/670; 514/731, 737

[56] References Cited

U.S. PATENT DOCUMENTS

| | | | |
|---|---|---|---|
| 1,596,651 | 8/1926 | Byant | 424/667 |
| 1,676,554 | 7/1928 | Hoopman | 424/667 |
| 1,767,667 | 6/1930 | Gray | 424/637 |
| 1,800,502 | 4/1931 | Brown | 424/667 |
| 1,896,171 | 2/1933 | Harry | 424/667 |
| 3,301,752 | 1/1967 | Bubash | 424/667 |
| 3,352,628 | 11/1967 | Starbuck | 422/37 X |
| 3,591,328 | 7/1971 | Szappanyos et al. | 422/37 X |
| 3,911,107 | 10/1975 | Krezanoski | 422/37 X |
| 4,006,218 | 2/1977 | Sipos | 424/54 |
| 4,081,396 | 3/1978 | Batterton | 252/99 X |
| 4,207,310 | 6/1980 | Langford | 424/670 |
| 4,290,846 | 9/1981 | Muntwyler | 162/161 |
| 4,321,257 | 3/1982 | Sipos | 424/78.06 |
| 4,444,756 | 4/1984 | Schüssler et al. | 424/605 |
| 4,766,113 | 8/1988 | West et al. | 514/187 |
| 4,903,583 | 2/1990 | Frazier | 422/306 X |
| 5,017,617 | 5/1991 | Kihara et al. | 514/635 |
| 5,154,920 | 10/1992 | Flesher et al. | 514/643 |
| 5,256,701 | 10/1993 | Tamara et al. | 514/781 |
| 5,379,806 | 1/1995 | Matthews et al. | 138/149 |

OTHER PUBLICATIONS

Board Decision on Appeal No. 93–0470, Ex parte Joseph Porcello, Apr. 10, 1993.

Block, Seymour S., Disinfection, Sterilization and Preservation, 2nd ed., 1977, pp. 662–663.

McCulloch, Ernest C., Disinfection and Sterilization, pp. 307–308, 1945.

Block, Seymour S., Disinfection, Sterilization and Preservation, 2nd ed., pp. 196–212, 1977.

McCullock, Ernest C., Disinfection and Sterilization, 2nd ed., pp. 345–346, 1945.

*Primary Examiner*—E. Leigh McKane
*Attorney, Agent, or Firm*—Ted W. Whitlock

[57] ABSTRACT

A composition and method for disinfecting inanimate and dermal skin surfaces includes phenol, iodine solution, and glycerine and water. In a most preferred embodiment, the solution includes, by volume, between about ½ and about 1 volume units phenol, between about ½ and about 2 volume units of iodine solution, between about 2 and about 8 volume units of glycerine. A suitable diluent such as water or glycerine can also be used. The iodine solution is preferably a tincture of iodine solution having, by volume, between about 2% and 10% iodine in ethyl alcohol, and about 5% potassium iodide.

10 Claims, No Drawings

METHOD FOR DISINFECTING DERMAL SURFACES AND INANIMATE SURFACES, AND PARTICULARLY AIR DUCTS

FIELD OF THE INVENTION

This invention relates generally to disinfectants, and more particularly to a disinfectant for dermal surfaces and inanimate surfaces such as air ducts.

BACKGROUND OF THE INVENTION

The presence of microbes such as bacteria are an ever-present problem for humans. Microbes are the cause of a variety of skin ailments.

Microbes can be transmitted through building air conditioning systems. The lack of ventilation in current building designs increases the likelihood that air-borne microbes will become circulated through the air ducts of a building. Filtration systems provided with the air-circulating systems do not always adequately remove these microbes from the circulating air. The rapid spread of bacteria and other microbes, causing ill health among building occupants, will likely result unless this condition is treated. The cycling of the air through the ducts allows microbes to settle on the inside surfaces of the ducts, particularly when air flow has stopped during an off cycle. Some of these microbes are picked up from the surface of the ducts when the flow of air resumes, and are passed out through the vents to reach the building occupants. It is therefore desirable to provide a method for controlling the spread of such microbes through building air conditioning and ventilation systems.

SUMMARY OF THE INVENTION

It is an object of the invention to provide a composition and method for disinfecting dermal surfaces, particularly through topical applications.

It is another object of the invention to provide a method for disinfecting inanimate surfaces such as metal, glass, ceramic and plastic, and particularly the interior surfaces of air ducts.

It is another object of the invention to provide a method which will help to control the transfer of microbes through HVAC duct systems.

These and other objects are accomplished by a composition and method in which a disinfecting composition comprising phenol, iodine, glycerine and water is provided. The composition is topically applied to inanimate surfaces and dermal surfaces. The composition will effectively disinfect the surfaces to control a number of microbe-associated problems.

The composition is also useful to disinfect the air ducts of heating, ventilation, and air conditioning (HVAC) systems. The solution can be misted by apparatus known in the art and caused to flow into the ducts, where it is carried by the flowing air through the ducts and deposited on interior duct surfaces. The glycerine coats the interior duct surfaces and retains the disinfecting phenol and iodine, such that microbes falling on the coating are killed and the transfer of microbes through the HVAC system is controlled. The composition can also be used to disinfect other inanimate objects such as laboratory instruments and instruments found in barber shops and beauty salons.

The composition can be applied to air ducts of many different designs, including metal, aluminum foil lined with glass-wool, and spiral ducts with a plastic filament. The glycerine will coat the interior surface of the duct to help to prevent unwanted corrosion and deterioration of the air duct. To ensure adhesiveness to the interior of the ducts, additional glycerine may be added. The composition can be released into the ducts through aerosol applicators such as those known as "foggers".

The composition can be applied to the skin by a variety of methods, including spray application or through the incorporation of other compounds as carriers for an ointment. It is also possible to add additional ingredients. The composition can be utilized in all suitable concentrations, and in all possible syncrases of the chemicals.

DETAILED DESCRIPTION OF THE PREFERRED EMBODIMENT

According to the invention, a method for disinfecting an inanimate surface, particularly air ducts, includes the steps of applying to the surface a disinfecting composition, including phenol, iodine, glycerine and water. The composition is applied to the surface by suitable methods, including brush application, aerosol, ointments or liquid pump.

In a preferred embodiment, a standard mixture is prepared which includes glycerine, phenol and tincture of iodine. The standard mixture comprises between approximately ½–1 volume unit of phenol (USP), between approximately ½–2 volume unit of 7% tincture of iodine solution (USP), and between approximately 2–8 volume units of glycerine (USP). Most preferably, the standard mixture comprises between about 2 and about 4 units of glycerine (USP). A currently preferred standard formula is as follows:

| | |
|---|---|
| Glycerine (USP) | 2 volume unit |
| 7% Tr. of Iodine (USP) | 1 volume unit |
| Phenol (USP) | 1 volume unit |

The standard mixture can be diluted up to about thirty times with suitable diluents such as water or additional glycerine, as well as mixtures of such diluents, based upon bactericidal demand. The final composition, if used for dermal applications, preferably contains less than about 1.0%, by volume, of phenol. One suitable composition that is useful for disinfecting inanimate surfaces is:

| | |
|---|---|
| Phenol (USP) | 1 oz. = 6.25% |
| 7% Tincture of iodine (USP) | 1 oz. = 6.25% |
| Glycerine (USP) | 4 oz. = 25% |
| Water (USP) | 10 oz. = 62.5% |

The concentration can be increased if a high bacteria count is present.

The composition has particular utility for disinfecting air ducts. In the preferred method, the composition is misted into the flowing air within the HVAC system where it is carried through the ducts and coats the inside surfaces of the ducts. It is possible to provide a misting system which will inject the composition into the flowing air only when the fan of the HVAC system is on and air is flowing through the ducts. A composition for disinfecting air ducts preferably comprises between about ½ and about 1 volume units phenol; between about ½ and about 2 volume units of iodine solution; between about 2 and about 8 volume units of glycerinee; and between about 10 and about 20 volume units of a diluent.

The iodine solution is preferably a tincture of iodine solution comprising, by volume, between about 2% and 10% iodine, about 5% potassium iodide (for stabilization), and the remainder ethyl alcohol. In a most preferred embodiment, the iodine solution is about 7% tincture of iodine (USP).

Compositions according to the invention can be applied to a surface by any suitable method. The application to air ducts can be made by any suitable means, as by a brush or roller, but is preferably atomized and propelled onto the surface by a pump or other suitable mode of force. In a most preferred embodiment, the atomized composition is injected into air flowing through the duct system, where it is carried and deposited throughout the interior surface of the duct.

The invention is suitable for air ducts of many different constructions, including metal, lined and spiral. Metal ducts are typically made of tin or aluminum. Lined ducts are typically glass-wool coated with aluminum foil. Spiral ducts typically have a plastic filament on the inside and outside. The invention is also suitable to disinfect other inanimate surfaces of metal, glass, ceramic or plastic, and for disinfecting air ducts in ships, hotels, hospitals, office buildings, and homes.

The invention also has utility for disinfecting dermal surfaces. The above-described composition can be applied to such skin surfaces to control microbe related problems such as pimples, canker sores, fever sores, herpes (genital and otherwise), and for local lavage of genitals after sexual intercourse to prevent sexual associated infections, for control and treatment of anal and perineal area infections, for control of local itchiness and pruritus, for control and treatment of intertrigo, for control and treatment of thrush, for control and treatment of gingivitis, and for pain abatement and control of infection associated with infected teeth.

In the application to dermal surfaces, the application can be made directly as an ointment, or by other suitable application methods known in the art. The invention can be used in different concentrations, and in all possible syncrases.

This invention can take other specific forms without departing from the spirit or essential attributes thereof, and accordingly, reference should be had to the following claims, rather than the foregoing specification, as indicating the scope of the invention.

I claim:

1. A method for disinfecting an inanimate surface, wherein said method is safe for the user, said method comprising the steps of:

providing a composition which is stingless, stainless, and non-irritative to skin or clothing, said composition consisting of, by volume of the total composition: about one volume units phenol; about one volume units 7% tincture of iodine solution; and about two volume units glycerine;

applying an effective amount of said composition to the inanimate surface to disinfect said surface.

2. The method of claim 1, wherein said composition further comprises a diluent.

3. The method of claim 2, wherein said diluent is selected from the group consisting of water and a mixture of water and additional glycerine.

4. The method of claim 3, wherein said diluent comprises between about 10 volume units and about 100 volume units.

5. The method of claim 1, wherein said surface is selected from the group consisting of glass, ceramic, metal, and plastic.

6. The method of claim 1, wherein prior to said application step, said composition is atomized.

7. The method of claim 6, wherein said atomized composition is propelled, whereby said surface will be evenly covered.

8. The method of claim 1, wherein said surface comprises an air duct.

9. The method of claim 8, wherein said air duct is selected from the group consisting of metal, aluminum foil lined with glass wool, and spiral ducts with a plastic filament.

10. A method for disinfecting air ducts, comprising the steps of:

providing a composition comprising between about ½ and about 1 volume units phenol; between about ½ and about 2 volume units of iodine solution; between about 2 and about 8 volume units of glycerinee; and between about 10 and about 20 volume units of a diluent;

atomizing said composition;

propelling said atomized composition through said air duct so as to coat an interior passage of said air duct with said composition.

* * * * *